United States Patent [19]

Schuster, Ludwig et al.

[11] Patent Number: 4,517,391

[45] Date of Patent: May 14, 1985

[54] CONTINUOUS PREPARATION OF ETHANOL

[75] Inventors: Schuster, Ludwig, Limburgerhof; Franz-Josef Mueller, Wachenheim; Axel Anderlohr, Mannheim; Peter Blei, Bad Durkheim; Gerhart Eigenberger; Bernd Höppner, both of Neustadt; Gerd Kaibel, Lampertheim; Wolfgang Steiner, Friedelsheim, all of Fed. Rep. of Germany

[73] Assignee: BASF Aktiengesellschaft, Ludwigshafen, Fed. Rep. of Germany

[21] Appl. No.: 496,573

[22] Filed: May 20, 1983

[30] Foreign Application Priority Data

Jun. 4, 1982 [DE] Fed. Rep. of Germany ....... 3221077

[51] Int. Cl.$^3$ ..................... C07C 29/136; C07C 31/08
[52] U.S. Cl. .................................................. 568/885
[58] Field of Search ......................................... 568/885

[56] References Cited

U.S. PATENT DOCUMENTS

| 2,607,807 | 8/1952 | Ford | 568/885 |
| 3,260,683 | 7/1966 | Endler | 568/885 |
| 3,478,112 | 11/1969 | Adam et al. | 568/885 |
| 3,708,534 | 1/1973 | Ishimoto et al. | 568/885 |
| 3,848,003 | 11/1974 | Mesich et al. | 568/885 |
| 3,855,319 | 12/1974 | Hobbs et al. | 568/885 |
| 4,113,662 | 9/1978 | Wall | 568/885 |
| 4,398,039 | 8/1983 | Pesa et al. | 568/885 |

FOREIGN PATENT DOCUMENTS

| 712197 | 6/1965 | Canada | 568/885 |
| 975134 | 11/1964 | United Kingdom | 568/885 |

OTHER PUBLICATIONS

J. Chem. Soc., vol. 77, (1955), pp. 3766-3767.
J. Org. Chem., vol. 2, (1959), pp. 1847-1854.

Primary Examiner—J. E. Evans
Attorney, Agent, or Firm—John H. Shurtleff

[57] ABSTRACT

Ethanol is prepared by hydrogenating acetic acid under superatmospheric pressure and at elevated temperatures by a process wherein a predominantly cobalt-containing catalyst is used and acetic acid and hydrogen are passed through the reactor, at from 210° to 330° C. and under from 10 to 350 bar, under conditions such that a liquid phase in not formed during this procedure.

13 Claims, No Drawings

CONTINUOUS PREPARATION OF ETHANOL

The present invention relates to an improved process for the continuous preparation of ethanol by catalytic hydrogenation of acetic acid with hydrogen under superatmospheric pressure and at elevated temperatures.

It is generally known that carboxylic acids can be catalytically hydrogenated to give the corresponding alcohols; however, it has not been possible hitherto to carry out the hydrogenation of acetic acid satisfactorily.

If ruthenium catalysts are used for this purpose (U.S. Pat. No. 2,607,807 and the corresponding paper in J. Chem. Soc. 77 (1955), 3766), the maximum yield is 88% in spite of the fact that an extremely high pressure of from 700–950 bar is employed; where a lower pressure of 200 bar is used, the yield obtained is 41%, which is quite unacceptable for industrial purposes.

The reaction with rhenium catalysts is just as unsatisfactory (J. Org. Chem. 23 (1959), 1850). In this process, the yield of ethanol is only about 40% (59% based on 68% conversion) in the most favorable case; moreover, to achieve this yield an uneconomically long residence time of 60 hours has to be accepted. If the reaction conditions are made harsher in order to achieve industrially reasonable residence times, the yield drops to 16%.

Apart from their poor results, the above processes also have the disadvantage that they require expensive catalysts. Development in the field of the hydrogenation of carboxylic acids has therefore subsequently been extended to include the use of cheaper catalysts, including, in particular, those containing cobalt as the essential component. Although higher carboxylic acids can be successfully hydrogenated to the alcohols using these catalysts, they do not permit hydrogenation of acetic acid, as can be seen indirectly from the relevant patent literature. Thus, German Patent No. 1,235,879 relates in general to the hydrogenation of carboxylic acids under superatmospheric pressure and at elevated temperatures in the presence of cobalt-containing catalysts, but the hydrogenation of acetic acid is not described in any of the fourteen examples.

A similar situation is found in the case of the process described in German Laid-Open Application DOS No. 1,921,848 (continuous hydrogenation of carboxylic acids with cobalt catalysts at 135°–350° C.), whose experimental part relates exclusively to the hydrogenation of pelargonic acid to nonanol. Even the process described in German Laid-Open Application DOS No. 2,321,101 (use of Co/Mo catalysts) is illustrated merely by the hydrogenation of a mixture of hydroxycaproic acid and adipic acid.

Although acetic acid is mentioned in the three last mentioned patent publications, its hydrogenation is not substantiated experimentally. The reason for this is not given, but it soon becomes evident when an attempt is made to hydrogenate acetic acid in accordance with the general methods described in the patent publications: under the harsh reaction conditions required, acetic acid is in fact so corrosive that it destroys the cobalt catalyst within a short time.

It is an object of the present invention to improve the hydrogenation of acetic acid by means of a cobalt-containing catalyst so that the above disadvantages are avoided and the process is hence economically viable for industry.

We have found that this object is achieved by a continuous process for the preparation of ethanol by hydrogenating acetic acid under superatmospheric pressure and at elevated temperatures, wherein a predominantly cobalt-containing catalyst is used and acetic acid and hydrogen are passed through the reactor, at from 210° to 330° C. and under from 10 to 350 bar, under conditions such that a liquid phase is not formed during this procedure.

The invention is based on the surprising observation that acetic acid, which in itself is extremely aggressive, loses its corrosive character virtually completely when it is in the gas phase. As a result, the process not only leaves the catalyst undamaged but also makes it unnecessary to use expensive metals or metal alloys as materials for the reactor or reactor accessories.

The proviso that a liquid phase be avoided during hydrogenation means that pressure and temperature must bear a certain functional relationship to one another. This function furthermore includes concentrations of all reactants and products (hydrogen, acetic acid, ethanol, water and ethyl acetate), which concentrations are in turn variable, depending on whether the mixture emerging from the reactor is recycled; it is therefore difficult to calculate the required pressure and temperature, especially since the formation of a liquid phase also depends on the flow behavior of the gas mixture. Instead, it is advisable to carry out a few preliminary experiments using an experimental apparatus which permits observation of the state of aggregation of the reaction mixture.

Since the reaction velocity increases with increasing pressure and increasing temperature, the reaction is preferably carried out under from 40 to 120 bar and at from 230° to 270° C. Above about 280° C., the formation of hydrocarbons, principally methane, becomes noticeable. At least in the upper pressure and temperature ranges, the reaction mixture is in a supercritical state, so that a liquid phase can no longer form.

The catalysts used should consist predominantly of cobalt, i.e. should contain no less than 50% by weight of cobalt. Although pure cobalt meets the requirements, further catalyst components, such as copper, manganese, chromium, molybdenum and phosphoric acid, have proved advantageous.

The catalysts, which have been disclosed in, for example, German Pat. No. 1,235,879, are prepared in a conventional manner from an appropriate mixture of metal oxides, with or without further components, e.g. phosphoric acid, by heating this mixture for a few hours in a stream of hydrogen; during this procedure, the major part of each of the oxides is reduced to the metal. In addition to the active components, the catalysts may also contain other, essentially inert materials, e.g. aluminum oxider or silica.

The catalysts may be employed with or without a carrier, the latter type being preferred. Supported catalysts are advantageously prepared by impregnating the carrier, preferably aluminum oxide or silica, once or repeatedly with an aqueous solution of the metal salts, preferably the nitrates. After impregnation and drying, the material is heated to convert the metal salts to the metal oxides, and these are then substantially reduced with hydrogen to the metals, as in the case of the unsupported catalysts.

Examples of suitable catalysts are those which contain, as active components, from 50 to 80% by weight of Co, from 10 to 30% by weight of Cu, from 0 to 10% by weight of Mn, from 0 to 5% by weight of Mo and from 0 to 5% by weight of phosphoric acid.

The amount of catalyst required for the hydrogenation depends on the reaction conditions and on its activity, which in turn is a function of the particle size and the surface area. For a fixed bed charge affording advantageous flow, it is advisable to use particles of 2-5 mm height and diameter, either in the form of an unsupported catalyst, or in the form of a supported catalyst containing from 10 to 20% by weight of active catalytic material.

With a charge of 1 liter of particles of this type, it is possible to hydrogenate about 0.1-0.7 kg per hour of acetic acid at 250° C. and under 100 bar.

A tube reactor may be used, but a tube-bundle reactor is preferred because it permits better temperature control. The very substantial heat of reaction can be conducted away by external cooling in the case of the tube-bundle reactor and by internal cooling with a cooling coil in the case of the tube reactor. If the latter is used, it may also be advisable to dilute the mixture of starting materials, i.e. hydrogen and acetic acid, with the mixture emerging from the reactor, this mixture being cooled in a conventional external cycle. The weight ratio of the recycled substances to fresh acetic acid is preferably from 1:1 to 2:1.

Preferably, hydrogen and acetic acid are passed through the reactor by co-current flow. It is advisable to introduce the acetic acid in gaseous form into the reactor, but it is also possible to introduce it in liquid form since it vaporizes instantly under the reaction conditions and as a result absorbs some of the heat of reaction. On the other hand, the catalyst should not come into contact with liquid acetic acid, and where this is used it is therefore advantageous if the reactor is not completely filled with the catalyst. The distance from the catalyst to the point at which the acetic acid is fed in can be determined from the rate of vaporization and the flow velocity.

Suitable reactor materials are standard stainless steels, e.g. ®V steels.

The process according to the invention permits virtually complete hydrogenation of the acetic acid, ethanol being obtained in a yield of above 95%. Some ethyl acetate, small amounts of other by-products and about 30% by weight, based on the acetic acid, of water are also obtained. The reaction mixture can be worked up in a conventional manner to obtain ethanol.

Within the framework of the efforts to obtain ethanol from methanol, carbon monoxide and hydrogen acetic acid, the novel process of the present invention succeeds in achieving an improvement in the critical step of the hydrogenation of acetic acid.

EXAMPLE

In a catalyst-filled experimental reactor which had a height of 2 m and an internal diameter of 4 cm and was lined with stainless steel, 0.5 kg per hour of glacial acetic acid was hydrogenated at 250° C. and under a total pressure of 300 bar (hydrogen partial pressure about 270 bar), the glacial acetic acid being passed into the reactor from above, together with 2.5 m³ (S.T.P.) of hydrogen. The charge, which was introduced in liquid form, vaporized instantly on entering the reactor, so that a liquid phase could not form at the catalyst bed. As was established in a model apparatus provided with a transparent window, it is impossible for a liquid phase to form under the stated reaction conditions.

The gases which emerged were cooled under pressure in an external condenser, and about 520 g per hour of liquid reaction mixture were obtained. This mixture comprised 68.2% by weight of ethanol, 29.0% by weight of water, 1.4% by weight of ethyl acetate, 0.5% by weight of n-butanol, 0.2% by weight of acetic acid and 0.7% by weight of other products.

This corresponds to an ethanol yield of 97%, which remained unchanged over the experimental periods of 30 days. This means that the activity of the catalyst remained constant in the procedure according to the invention.

The catalyst charge had a volume of about 1.6 liters and reached a height of about 130 cm in the reactor. The catalyst, which comprised extrudates having a diameter of 4 mm and a height of 3-6 mm, was converted to the active form before hydrogenation was carried out. To achieve this conversion, 3,950 g of the oxide particles (CoO, CuO, $Mn_3O_4$ and $MoO_3$) were heated for 48 hours at 350° C. in an $H_2/N_2$ stream, and the major part of the catalyst was converted to the metallic form. The catalyst contained 71% by weight of Co, 18.5% by weight of Cu, 7.5% by weight of Mn and 3% by weight of Mo, the percentages being based on the metal content.

COMPARATIVE EXPERIMENT

At 200° C. and under a pressure of 400 bar, but under otherwise identical conditions, model considerations showed that a liquid phase must by present. The ethanol yield in this case was only 81%, but dropped to 63% in the course of only 5 days.

We claim:

1. In a process for the continuous catalytic preparation of ethanol by hydrogenating acetic acid under superatmospheric pressure and at an elevated temperature, the improvement which comprises:
    carrying out the hydrogenation in a reactor using a catalyst consisting of: either
    (a) Cobalt;
    (b) Cobalt and an essentially inert carrier;
    (c) No less than 50% Cobalt plus one or more members selected from the group consisting of copper manganese, molybdenum, chromium and phosphoric acid; or
    (d) an essentially inert carrier and an active component which is no less than 50% cobalt plus one or more members selected from the group consisting of copper manganese, molybdenum, chromium and phosphooric acid; and 2. A process as claimed in claim 1, wherein the pressure is from 40 to 120 bar and the temperature is from 230° to 270° C.

3. A process as claimed in claim 1 wherein the active component of (d) contains from 50 to 80% by weight of cobalt, from 10 to 30% by weight of copper, from 0 to 10% by weight of manganese, from 0 to 5% by weight of molybdenum and from 0 to 5% by weight of phosphoric acid.

4. A process as claimed in claim 1 wherein hydrogen and acetic acid are passed through the reactor in co-current flow for contact with said catalyst.

5. A process as claimed in claim 2 wherein hydrogen and acetic acid are passed through the reactor in co-current flow for contact with said catalyst.

6. A process as claimed in claim 4 wherein the acetic acid is introduced in gaseous form into the reactor.

7. A process as claimed in claim 15 wherein the acetic acid is introduced in gaseous form into the reactor.

8. A process as claimed in claim 1 comprising, recycling at least a part of the reaction products.

9. A process as claimed in claim 8 wherein the reaction temperature is from 230° to 270° C. and the reaction pressure is from 40 to 120 bar.

10. A process as claimed in claim 8 wherein the weight ratio of the recycled reaction products to fresh acetic acid is about 1:1 to 2:1.

11. A process as claimed in claim 9 wherein the weight ratio of the recycled reaction products to fresh acetic acid is about 1:1 to 2:1.

12. A process as claimed in claim 8 wherein the catalyst is used in the reactor in the form of particles of 2-5 mm in height and diameter.

13. A process as claimed in claim 5 wherein the catalyst is used in the form of a supported catalyst containing about 10-20% by weight of active components on an inert carrier.

* * * * *

UNITED STATES PATENT AND TRADEMARK OFFICE
CERTIFICATE OF CORRECTION

PATENT NO. : 4,517,391
DATED : May 14, 1985
INVENTOR(S) : Ludwig Schuster et al.

It is certified that error appears in the above-identified patent and that said Letters Patent is hereby corrected as shown below:

Claim 1, in the last line, after "and" add the phrase:

-- passing acetic acid and hydrogen through the reactor at a temperature of from 210 to 330°C and at a pressure of from 10 to 350 bar, under conditions such that a liquid phase is not formed by the reaction mixture during this procedure. --

Claim 7, line 1: change the numeral "15" to -- 5 --.

Claim 8, line 1: after "comprising" delete the comma (,).

Claim 13, line 1: change the numeral "5" to -- 12 --.

Signed and Sealed this

Fifth Day of November 1985

[SEAL]

Attest:

Attesting Officer

DONALD J. QUIGG

Commissioner of Patents and Trademarks